US006352978B1

(12) United States Patent
Perdiguer et al.

(10) Patent No.: US 6,352,978 B1
(45) Date of Patent: Mar. 5, 2002

(54) PHARMACEUTICAL COMPOSITIONS CONTAINING TOBRAMYCIN AND XANTHAN GUM

(75) Inventors: Nuria Carreras Perdiguer; Jose Alberto Vallet Mas; Gemma Torrella Cabello, all of Barcelona (ES)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/902,844

(22) Filed: Jul. 11, 2001

Related U.S. Application Data
(60) Provisional application No. 60/221,660, filed on Jul. 28, 2000.

(51) Int. Cl.$^7$ .................. A61K 31/70; A61K 31/35; A61K 31/74
(52) U.S. Cl. ................. 514/37; 514/35; 514/912; 514/460; 424/78.04
(58) Field of Search ................ 514/460, 912, 514/35, 37; 424/78.04

(56) References Cited

U.S. PATENT DOCUMENTS

| | | | |
|---|---|---|---|
| 3,700,451 A | 10/1972 | Sullivan, Jr. | 96/66 |
| 3,784,712 A | 1/1974 | Glicksman et al. | 426/167 |
| 3,944,427 A | 3/1976 | Sullivan, Jr. | 106/208 |
| 4,135,979 A | 1/1979 | Corley et al. | 195/31 |
| 4,136,173 A | 1/1979 | Pramoda et al. | 424/177 |
| 4,136,177 A | 1/1979 | Lin et al. | 424/211 |
| 4,136,178 A | 1/1979 | Lin et al. | 424/211 |
| 4,638,059 A | 1/1987 | Sutherland | 536/121 |
| 4,647,470 A | 3/1987 | Sanderson et al. | 426/573 |
| 4,661,475 A | 4/1987 | Bayerlein et al. | 514/54 |
| 4,708,861 A | 11/1987 | Popescu et al. | 424/1.1 |
| 4,717,713 A | 1/1988 | Zatz et al. | 514/2 |
| 4,775,632 A | 10/1988 | Gozard et al. | 435/104 |
| 4,861,760 A | 8/1989 | Mazuel et al. | 514/54 |
| 4,996,197 A | 2/1991 | Mazuel | 514/54 |
| 5,149,694 A | 9/1992 | Cagle et al. | 424/81 |
| 5,192,535 A | 3/1993 | Davis et al. | 424/78.04 |
| 5,212,162 A | 5/1993 | Missel et al. | 514/54 |
| 5,234,957 A | 8/1993 | Mantelle | 514/772.6 |
| 5,318,780 A | 6/1994 | Viegas et al. | 424/427 |
| 5,403,841 A | 4/1995 | Lang et al. | 514/226.8 |
| 5,422,116 A | 6/1995 | Yen et al. | 424/427 |
| 5,446,070 A | 8/1995 | Mantelle | 514/772.6 |
| 5,461,081 A | 10/1995 | Ali et al. | 514/772.3 |
| 5,462,749 A | 10/1995 | Rencher | 424/484 |
| 5,473,062 A | 12/1995 | Haze et al. | 536/114 |
| 5,493,015 A | 2/1996 | Murofushi et al. | 536/127 |
| 5,587,175 A | 12/1996 | Viegas et al. | 424/427 |
| 5,610,184 A | 3/1997 | Shahinian, Jr. | 514/540 |
| 5,618,800 A | 4/1997 | Kabra et al. | 514/57 |
| 5,679,336 A | 10/1997 | Ali et al. | 424/78.04 |
| 5,759,563 A | 6/1998 | Yewey et al. | 424/426 |
| 5,888,493 A | 3/1999 | Sawaya | 424/78.04 |
| 6,174,524 B1 * | 1/2001 | Bawa et al. | |
| 6,294,186 B1 * | 9/2001 | Beerse et al. | |
| 6,297,337 B1 * | 10/2001 | Marchant et al. | |

FOREIGN PATENT DOCUMENTS

| | | |
|---|---|---|
| CA | 1070629 | 1/1980 |
| EP | 0 331 617 A1 | 9/1989 |
| EP | 0 374 658 A2 | 12/1989 |
| EP | 0 410 326 A2 | 7/1990 |
| EP | 0 424 043 A1 | 10/1990 |
| EP | 0 424 043 B1 | 5/1993 |
| EP | 0 780 121 A1 | 12/1996 |
| WO | 96/03990 | 2/1996 |
| WO | 98/11874 | 3/1998 |
| WO | 98/17249 | 4/1998 |
| WO | 98/41171 | 9/1998 |
| WO | 98/53809 | 12/1998 |
| WO | 99/00133 | 1/1999 |
| WO | 99/51273 | 10/1999 |

OTHER PUBLICATIONS

Carrington et al., "Polyelectrolyte Behaviour of Dilute Xanthan Solutions: Salt Effects on Extensional Rheology," *Polymer*, vol. 37 (13); pp. 2871–2875 (1996).

Foss et al., "Thermal Stability and Chain Conformational Studies of Xanthan at Different Ionic Strengths," *Carbohydrate Polymers*, vol. 7, pp. 421–433 (1987).

Gamini et al., "Physico–chemical Properties of Aqueous Solutions of Xanthan: An n.m.r. Study," *Carbohydrate Research*, vol. 220, pp. 33–47 (1991).

Kelco Product Brochure, "Xanthan Gum—Natural Biogum for Scientific Water Control," Fifth Edition (1994).

Kierulf et al., "Thermal Stability of Xanthan Preparations," *Carbohydrate Polymers*, vol. 9, pp. 185–194 (1988).

Lambert et al., "On the Thermal Stability of Xantha Gum," *Polymer*, vol. 26, pp. 1549–1553 (1985).

Lund et al., Properties of Xanthan Solutions after Long–Term Heat Treatment at 90° C, *Polymer Degradation and Stability*, vol. 27, pp. 211–225 (1990).

McNeely et al., *Industrial Gums*, Academic Press, Inc., San Diego, CA, (1973), Chapter VII. "Xantham Gum," pp. 486–497.

Meseguer et al., "Gamma Scintigraphic Comparison of Eyedrops Containing Pilocarpine in Healthy Volunteers," *J. of Ocular Pharmacology and Therapeutics*, vol. 12(4), pp. 481–488 (1996).

(List continued on next page.)

Primary Examiner—William R. A. Jarvis
Assistant Examiner—Vickie Kim
(74) Attorney, Agent, or Firm—Patrick M. Ryan

(57) ABSTRACT

Topically administrable aqueous solution compositions containing tobramycin and xanthan gum are disclosed. The solution compositions contain a buffering agent and a pH-adjusting agent in an amount sufficient to achieve a pH above 7.8 in order to minimize or avoid compatibility problems between tobramycin and xanthan gum.

12 Claims, No Drawings

OTHER PUBLICATIONS

Meseguer et al., "Gamma Scintigraphic Study of Precorneal Drainage and Assessment of Miotic Response in Rabbits of Various Ophthalmic Formulations Containing Pilocarpine," *International J. of Pharmaceutics*, vol. 95, pp. 229–234 (1993).

Milas et al., "The Effect of Thermal Aging on Xanthan Solutions," *J. of Applied Polymer Science*, vol. 35, pp. 1115–1122 (1988).

Nolte et al., "Gelation of Xanthan With Trivalent Metal Ions," Carbohydrate Polymers, vol. 18 (4), pp. 243–251 (1992).

Oviatt et al., "Thermal Treatment of Semi–dilute Aqueous Xanthan Solutions Yields Weak Gels with Properties Resembling Hyaluronic Acid," *Int. J. Biol. Macromol.*, vol. 15(3), pp. 3–10, 1992.

Sanford et al., "Microbial Polysaccharides: New Products and Their Commercial Applications," *Pure & Appl. Chem.*, vol. 56(7), pp. 879–892 (1984).

Shatwell et al., "The Influence of Acetyl and Pyruvate Substitutents on the Helix—Coil Transition Behaviour or Xanthan," Carbohydrate Research, vol. 206 (1), pp. 87–103 (1990).

Smith et al., "Influence of the Pyruvate Content of Xanthan on Macromolecular Association in Solution," *Int. J. Biol. Macromol.*, vol. 3, pp. 129–134 (1981).

Tait et al., "Acid Hydrolysis and High–Perfomance Liquid Chromatography of Xanthan," *Carbohydrate Polymers*, vol. 13, pp. 133–148 (1990).

Tobramycin, *Merck Index* $12^{th}$ Edition, Merck Research Laboratories, Whitehouse Station, NJ, (1996) p. 1619.

* cited by examiner

PHARMACEUTICAL COMPOSITIONS CONTAINING TOBRAMYCIN AND XANTHAN GUM

This application claims priority from co-pending U.S. Provisional Application, U.S. Ser. No. 60/221,660, filed Jul. 28, 2000.

BACKGROUND OF THE INVENTION

1. Field of the Invention

The present invention relates to pharmaceutical compositions suitable for topical administration to the eye, ear or nose. In particular, this invention relates to pharmaceutical compositions formulated so that tobramycin and xanthan gum are compatible.

2. Description of Related Art

Xanthan gum is a polysaccharide known to be useful in ophthalmic compositions as a viscosity-enhancing agent. U.S. Pat. No. 4,136,177 discloses ophthalmic compositions containing an ophthalmic drug and from about 0.01 to 2.5% (w/v) of xanthan gum. The '177 patent teaches that if the concentration of xanthan gum is from about 0.02 to about 1.0% (w/v), the composition is suitable for "dropwise" ophthalmic applications In contrast, at concentrations of xanthan gum above about 1.0% and up to about 2.5% (w/v), "a gel-like consistency is attained." Thus, the '177 patent discloses compositions that are formulated to be either non-gelled liquids or gels before instillation in the eye. The '177 patent does not describe any xanthan gum-containing compositions as capable of being administered as a liquid and gelling upon contact with the eye. According to the '177 patent, any ophthalmic drug can be added to the xanthan gum-containing compositions. The '177 patent does not include tobramycin when it lists examples of suitable antibacterial drugs (see Col. 3, lines 54–58).

WO 99/51273 discloses gel-forming compositions containing xanthan gum where the xanthan gum has an initial bound acetate content of at least about 4% and an initial bound pyruvate content of at least about 2.5%. The entire contents of WO 99/51273 are hereby incorporated by reference.

Tobramycin is an antibiotic drug known to be useful in pharmaceutical compositions. For example, a TOBREX® brand of tobramycin ophthalmic solution and ointment products is marketed by Alcon Laboratories, Inc. (Fort Worth, Tex.).

SUMMARY OF THE INVENTION

The present invention is directed toward pharmaceutical aqueous solutions of tobramycin and xanthan gum that are topically administrable to the eye, ear or nose. According to the present invention, the solution compositions are formulated at a certain pH in order to minimize or eliminate compatibility problems between tobramycin and xanthan gum. The solution compositions have a pH greater than 7.8.

Among other factors, the present invention is based upon the finding that 0.3% tobramycin and 0.6% xanthan gum are incompatible at pH 5–7.8 despite the fact that both tobramycin and xanthan gum are independently sufficiently soluble in aqueous solution to give 0.3% and 0.6% solutions, respectively, but are compatible at a pH greater than 7.8.

DETAILED DESCRIPTION OF THE INVENTION

Unless otherwise indicated, all ingredient concentrations are listed as % (W/V).

Xanthan gum is a well-known polysaccharide that is commercially available from a variety of sources. The amount of xanthan gum contained in the compositions of the present invention will depend upon the properties desired for the final composition and the identity and concentration of other ingredients in the composition, but will generally range from about 0.4 to about 0.8%, preferably 0.5–0.7%. Most preferred is a xanthan gum concentration of about 0.6%.

Xanthan gum is generally available in at least two grades from some commercial suppliers, a food or industrial grade and a pharmaceutical grade. Even pharmaceutical grade materials should be polish-filtered so that the finished pharmaceutical product will have increased clarity. As one skilled in the art appreciates, the appropriate filter size for polish filtration depends upon the size of the undesired impurities contained in raw material. For example, in the case of a solution composition, it has been found that the Rhodigel Clear grade of xanthan gum from Rhone-Poulenc Inc. should be filtered through a 0.45 $\mu$m filter in order to remove cell debris and impurities. Multiple stages of filters can be used to increase the overall efficiency of the polish filtration process.

Tobramycin is a known antibiotic drug. See, for example, The Merck Index, Twelfth Edition, page 1619. The concentration of tobramycin in the solution compositions of the present invention will generally be about 0.5% or less. In topically administrable ophthalmic compositions, the preferred concentration of tobramycin is 0.3%.

In addition to xanthan gum and tobramycin, the solution compositions of the present invention contain a buffer agent and a pH-adjusting agent so that the pH is above 7.8. Preferably, the pH of the solution compositions is about 7.9–8.6, more preferably, 7.9–8.2, and most preferably 8.0. Suitable buffering agents include tromethamine; phosphate and borate. The most preferred buffering agent is tromethamine. Suitable pH-adjusting agents include sulfuric acid and hydrochloric acid. The most preferred pH-adjusting agent is sulfuric acid.

The solution compositions of the present invention may include other components. For example, the compositions may include a second active agent (not limited to anti-infective agents). The compositions may also contain one or more pharmaceutically acceptable excipients, including, but not limited to, preservatives (including preservative adjuncts), tonicity-adjusting agents including salts containing monovalent cations, surfactants, solubilizing agents, stabilizing agents, comfort-enhancing agents, emollients, agents and lubricants.

The following examples are presented to illustrate further various aspects of the present invention, but are not intended to limit the scope of the invention in any respect.

EXAMPLES

Example 1

Each of the formulations shown in Table 1 was prepared as follows. To the required amount of xanthan gum solution (obtained from a polish-filtered stock solution), the remaining ingredients indicated for Part A were added. Tromethamine was added from a 2% stock solution (Formulation #'s 4 and 7) or in the form of a powder (all other Formulations). L-Lysine was added from a 50% stock solution. The formulations were then autoclaved at 124 ° C. for 45 minutes. After autoclaving, the required amount of tobramycin was added (from a 2.5% stock solution of tobramycin containing sulfuric acid so that the pH was 8.4–8.5). Purified water and additional sulfuric acid, if necessary, were added to achieve final batch size and target pH.

TABLE 1

| INGREDIENT | FORMULATION # | | | | |
|---|---|---|---|---|---|
| | 1 | 2 | 3 | 4 | 5 |
| Part A: | | | | | |
| Xanthan Gum | 0.6 | 0.6 | 0.6 | 0.6 | 0.6 |
| Mannitol | — | — | — | — | 4.5 |
| Tromethamine | — | — | — | q.s. to pH 8.35 | 0.9 |
| L-Lys | — | — | q.s. to pH 9.54 | — | — |
| NaOH 1N | q.s. to pH 8.58 | q.s. to pH 8.58 | — | — | — |
| Boric Acid | — | — | — | — | 0.3 |
| Benzododecinium Bromide | — | — | — | — | 0.012 |
| Part B: | | | | | |
| 2.5% Tobramycin (+$H_2SO_4$ q.s. pH 8.4–8.5) | 0.3 | 0.3 | 0.3 | 0.3 | 0.3 |
| Final pH | pH 5.65 | pH 7.27 | pH 7.76 | pH 7.80 | pH 8.12 |
| Purified Water | q.s. to 100 | q.s. to 100 | q.s. to 100 | q.s. to 100 | q.s. to 100 |
| Result: | | | | | |
| Precipitation | Yes | — | — | — | — |
| White Filaments* | — | Yes | Yes | Yes | — |
| Clear & Colorless | — | — | — | — | Yes |

| INGREDIENT | FORMULATION # | | | | |
|---|---|---|---|---|---|
| | 6 | 7 | 8 | 9 | 10 |
| Part A: | | | | | |
| Xanthan Gum | 0.6 | 0.6 | 0.6 | 0.6 | 0.6 |
| Mannitol | 4.5 | — | 3.75 | — | — |
| Tromethamine | 1.0 | q.s. to pH 8.35 | 1.2 | — | — |
| L-Lys | — | — | — | q.s. to pH 9.54 | — |
| NaOH 1N | — | — | — | — | q.s. to pH 8.58 |
| Boric Acid | 0.3 | — | 0.3 | — | — |
| Benzododecinium Bromide | 0.012 | — | 0.012 | — | — |
| Part B: | | | | | |
| 2.5% Tobramycin (+$H_2SO_4$ q.s. pH 8.4–8.5) | 0.3 | 0.3 | 0.3 | 0.3 | 0.3 |
| Final pH | pH 8.15 | pH 8.36 | pH 8.40 | pH 8.44 | pH 8.57 |
| Purified Water | q.s. to 100 | q.s. to 100 | q.s. to 100 | q.s. to 100 | q.s. to 100 |
| Result: | | | | | |
| Precipitation | — | — | — | — | |
| White Filaments* | — | — | — | — | |
| Clear & Colorless | Yes | Yes | Yes | Yes | Yes |

*White filaments disappeared after stirring

A representative compound procedure is listed below for Formulation #8.

1. Tare a suitable container, pour the required amount of purified water and heat to about 70° C. in a water bath.
2. Weigh out and slowly add the required amount of xanthan gum with stirring to prepare a stock solution of 0.8%, by using an overhead mixer with a suitable blade.
3. Allow the xanthan gum to hydrate for 1 hour, maintaining the temperature at 70° C.
4. Adjust water to volume and clarify the stock solution: filter through a 1.2$_\mu$ prefilter at pressure 1–1.5 kg/cm$^2$ maintaining the unfiltered stock solution and the filter and the receiving vessel at high temperature. Filter through a 0.45$_\mu$ final filter at pressure about 3 kg/cm$^2$. It is recommended to perform filtration in two steps since a lack of pressure may occur in the second filter, if a clarifying filter set-up is used, and the process slows down.
5. Tare a suitable container and weigh in the appropriate amount of clarified xanthan gum stock solution.
6. Weight out and add mannitol with vigorous stirring. Allow to fully dissolve with stirring.
7. Separately, weigh out and dissolve an appropriate amount of purified water boric acid with vigorous stirring. Allow to fully dissolve with stirring (magnetic stirring).
8. Weight out and add to the previous solution (step 7) tromethamine. Allow to fully dissolve with stirring.
9. Weigh out and add Polysorbate 80 to the solution of step 8. Allow to fully dissolve with stirring.
10. Weigh out and add benzododecinium bromide to the solution of step 9. Allow to fully dissolve with stirring.
11. Add the resulting solution of step 10, prefiltered through a polishing filter, to the vessel containing the xanthan gum and mannitol mixture. Allow to fully incorporate with stirring (overhead mixer).
12. Adjust to volume with purified water and transfer to a suitable bottle (tare full with magnetic bar inside and close the vessel).
13. Autoclave at 124° C. for 45 min and allow to cool to room temperature.
14. Separately, weigh out and add tobramycin to the appropriate amount of purified water (2.5% stock solution). Allow to fully dissolve with stirring.

15. Adjust to pH 8.4 by slowly adding sulfuric acid.
16. Aseptically add the tobramycin solution obtained in step 15 to the first portion of the formulation after sterile filtration, with stirring. Stir until homogeneous.
17. Adjust to final weight of the formulation with sterile purified water.

Example 2

Each of the formulations shown in Table 2 was prepared according to the method described in Example 1.

TABLE 2

| Ingredient | Formulation # | | |
|---|---|---|---|
| | 11 | 12 | 13 |
| Tobramycin | 0.30 g + 5% excess | 0.30 g + 5% excess | 0.30 g + 5% excess |
| Xanthan Gum | 0.60 g | 0.60 g | 0.60 g |
| Mannitol | 3.75 g | 3.75 g | 3.75 g |
| Boric Acid | 0.30 g | 0.30 g | 0.30 g |
| Polysorbate 80 | — | 0.05 g | 0.05 g |
| Tromethamine | 1.20 g | 1.20 g | 1.20 g |
| Benzododecinium Bromide | 0.012 g | 0.012 g | 0.012 g |
| Edetate Disodium | — | — | 0.05 g |
| Sulfuric Acid | q.s. to pH 8.3 | q.s. to pH 8.3 | q.s. to pH 8.3 |
| Purified Water | q.s. to 100 g | q.s. to 100 g | q.s. to 100 g |

All three formulations shown in Table 2 were placed on stability (25±2° C./40% R.H. and 40±2° C./15% R.H.) for six months. All three formulations showed no sign of precipitation or tobramycin/xanthan gum compatibility problems.

Example 3

Each of the formulations shown in Table 3 was prepared as follows. A solution of xanthan gum (from a clarified stock solution), mannitol, tromethamine, benzododecinium bromide and purified water was prepared, forming approximately 87% of the final batch weight. This portion was autoclaved at 121° C. for 45 minutes. Separately, a solution of tobramycin in purified water was prepared and sulfuric acid added to obtain the indicated target pH. This tobramycin portion was sterilized by sterile filtration (0.2 $\mu$m) before being combined with the xanthan gum portion of the formulation.

No precipitation was observed in any of the three formulations shown in Table 3. Each of the three formulations was evaluated against reference solutions of the European Pharmacopoeia (3rd edition; 1997) for clarity using the following scale: RS I (clearest)–RS IV (least clear). The clarity rating difference between Formulation #14 on the one hand and Formulation #15 and 16 on the other could indicate a future precipitation or tobramycin/xanthan gum compatibility problem.

TABLE 3

| Ingredient | Formulation # | | |
|---|---|---|---|
| | 14 | 15 | 16 |
| Tobramycin | 0.30 g + 5% excess | 0.30 g + 5% excess | 0.30 g + 5% excess |
| Xanthan Gum | 0.60 g | 0.60 g | 0.60 g |
| Mannitol | 3.75 g | 3.75 g | 3.75 g |
| Boric Acid | 0.30 g | 0.30 g | 0.30 g |
| Polysorbate 80 | 0.05 g | 0.05 g | 0.05 g |
| Tromethamine | 1.00 g | 0.75 g | 0.65 g |
| Benzododecinium Bromide | 0.012 g | 0.012 g | 0.012 g |
| Sulfuric Acid | q.s. to pH 8.0 | q.s. to pH 7.6 | q.s. to pH 7.1 |
| Purified Water | q.s. to 100 g | q.s. to 100 g | q.s. to 100 g |
| Clarity | ≦RS III | ≦RS IV | ≦RS IV |

Example 4

Formulation #s 4 and 8 were prepared as described in Example 1 and then divided into three portions. Sulfuric acid was added to each portion to adjust the pH to approximately 7.0, 7.4 and 7.8, respectively. White filaments were observed when the sulfuric acid was added, but these filaments disappeared after stirring. Each of the formulations was stored at 4° C. Samples were analyzed for clarity (nephelos testing) after 11, 18 and 35 days. The results (in NTU) are shown in Table 4.

TABLE 4

| Formulation # | Initial | | 11 Days | | 18 Days | | 35 Days | |
|---|---|---|---|---|---|---|---|---|
| | pH | NTU | pH | NTU | pH | NTU | pH | NTU |
| 4 | 7.85 | 14.7 | 7.66 | 11.8 | 7.67 | 13.4 | — | — |
| 4 | 7.41 | 34.1 | 7.36 | 38.4 | 7.23 | 48.6 | 7.33 | 71.9 |
| 4 | 7.05 | 223 | 7.01 | 302 | 6.87 | 884 | — | — |
| 8 | 7.84 | 14.7 | 7.76 | 18.2 | 7.72 | 15.7 | 7.91 | 14.2 |
| 8 | 7.45 | 19.9 | 7.42 | 21.4 | 7.33 | 39.3 | — | — |
| 8 | 7.02 | 28.9 | 6.98 | 31.4 | 6.90 | 96.4 | — | — |

Xanthan gum and tobramycin incompatibility becomes greater as final pH decreases since higher NTU values may indicate a problem of future precipitation.

Example 5

A preferred solution composition according to the present invention is shown in Table 5.

TABLE 5

| Ingredient | Amount (% w/v) |
|---|---|
| Tobramycin | 0.30 + 5% excess |
| Xanthan Gum | 0.60 |
| Mannitol | 3.75 |
| Boric Acid | 0.30 |

TABLE 5-continued

| Ingredient | Amount (% w/v) |
| --- | --- |
| Polysorbate 80 | 0.05 |
| Tromethamine | 1.00 |
| Benzododecinium Bromide | 0.012 + 5% excess |
| Sulfuric Acid | q.s. to pH 8.0 |
| Purified Water | q.s. to 100 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A topically administrable solution composition comprising tobramycin, xanthan gum, a buffering agent and a pH-adjusting agent, wherein the composition has a pH greater than pH 8.0.

2. The composition of claim 1 wherein the composition has a pH of about 8.6 or less.

3. The composition of claim 2 wherein the composition has a pH of about 8.2 or less.

4. The composition of claim 1 wherein tobramycin is present in an amount of about 0.5%(w/v) or less and xanthan gum is present in an amount of about 0.4–0.8%(w/v).

5. The composition of claim 1 wherein the buffering agent is tromethamine and the pH-adjusting agent is sulfuric acid.

6. The composition of claim 1 wherein the composition further comprises one or more ingredients selected from the group consisting of active agents; preservatives; tonicity-adjusting agents; surfactants; solubilizing agents; stabilizing agents; comfort-enhancing agents; emollients; and lubricants.

7. A topically administrable solution composition consisting essentially of tobramycin, xanthan gum, tromethamine, sulfuric acid, mannitol, boric acid, polysorbate 80, benzododecinium bromide, and purified water, wherein the composition has a pH of about 7.9–8.2.

8. A method of increasing the stability of an aqueous solution composition comprising xanthan gum, a buffering agent, a pH-adjusting agent and a drug consisting essentially of tobramycin, wherein the method comprises preparing the composition such that it has a pH from 7.9–8.6.

9. The method of claim 8 wherein the method comprises preparing the composition such that it has a pH from 7.9–8.2.

10. The method of claim 8 wherein the composition comprises tobramycin in an amount of about 0.6%(w/v) or less and xanthan gum in an amount of about 0.4–0.8 %(w/v).

11. The method of claim 8 wherein the buffering agent is tromethamine and the pH-adjusting agent is sulfuric acid.

12. The method of claim 8 wherein the composition further comprises one or more ingredients selected from the group consisting of active agents; preserves; tonicity-adjusting agents; surfactants; solubilizing agents; stabilizing agents; comfort-enhancing agents; emollients; and lubricants.

* * * * *